(12) United States Patent
Chuang et al.

(10) Patent No.: US 6,176,141 B1
(45) Date of Patent: Jan. 23, 2001

(54) METHOD FOR STUD PULL TEST FOR FILM FORMED ON SEMICONDUCTOR DEVICE

(75) Inventors: Lung-Hsiang Chuang, Shiao-Chia; Chung-Long Chang, Dou-Liu; Syun-Ming Jang; Ying-Chen Chao, both of Hsin-Chu, all of (TW)

(73) Assignee: Taiwan Semiconductor Manufacturing Company, Hsin-Chu (TW)

( * ) Notice: Under 35 U.S.C. 154(b), the term of this patent shall be extended for 0 days.

(21) Appl. No.: 09/332,379

(22) Filed: Jun. 14, 1999

(51) Int. Cl.[7] ..................................... G01N 3/00
(52) U.S. Cl. .............................. 73/838; 73/150 A
(58) Field of Search .................... 73/827, 830, 831, 73/834, 835, 838, 150 A

(56) References Cited

U.S. PATENT DOCUMENTS

| | | | |
|---|---|---|---|
| 4,856,326 | * 8/1989 | Tsukamoto | 73/150 A |
| 4,876,896 | 10/1989 | Snow et al. | 73/827 |
| 4,895,028 | 1/1990 | Mayer | 73/827 |
| 4,899,581 | * 2/1990 | Allen et al. | 73/150 A |
| 5,337,614 | 8/1994 | Jiang et al. | 73/827 |
| 5,673,586 | * 10/1997 | Mann | 73/150 A |

* cited by examiner

Primary Examiner—Max Noori
(74) Attorney, Agent, or Firm—George O. Saile; Stephen B. Ackerman; William Robertson

(57) ABSTRACT

A test sample with a film and an underlying substrate representing part of a semiconductor wafer is prepared for a stud pull test by a process that includes maintaining the sample in boiling salt water for a few hours. When an epoxy stud is attached to the film of the sample and the clamped assembly is baked for a about an hour, the stud is firmly attached to the film and in an otherwise conventional pull test, the film breaks loose from the substrate (or the stud breaks from the epoxy) before the stud breaks from the film.

11 Claims, 2 Drawing Sheets

METHOD FOR STUD PULL TEST FOR FILM FORMED ON SEMICONDUCTOR DEVICE

FIELD OF THE INVENTION

This invention relates generally to testing the adhesion of a film to its underlying structure in a semiconductor wafer, and more specifically it relates to an improved test sample and method for preparing the test sample.

1. Introduction

Semiconductor chips are commonly formed of multiple layers of conductors and dielectrics, for example a film of a dielectric material formed on an underlying structure. It is desirable to test the adhesion of such a film to the underlying structure. This test can be performed on an actual semiconductor device or on a sample that is made to adequately represents the film and underlying structure of the semiconductor device.

2. The Prior Art

U.S. Pat. No. 4,876,896 teaches testing the adhesion of a grouting to an underlying pier. A circular groove is cut through the grouting to isolate a circular test region. A part 42, 42a is attached to the outer surface of the test region. A screw mechanism applies a pulling force to the attached part, and a bridge applies a corresponding force to the structure outside the circular groove. The screw is calibrated to show the force.

U.S. Pat. No. 4,895,028 teaches apparatus for pulling on a wire that is bonded at each end to bonding pads of an integrated circuit device. The force is measured with a strain gauge and a computer calculates the force on the bonds.

U.S. Pat. No. 5,337,614 teaches an apparatus for grasping a circuit module and a heat sink attached to the module for an adhesion test.

In the manufacturing art to which this invention is particularly intended, tests for adhesion have been made after the wafer has been completed and formed into modules.

In another example of an adhesion test in this art, a stud has been attached to a film formed on a test sample and then the stud has been pulled from the sample until the film breaks loose from its underlying structure. Unfortunately, the stud may break from the film before the film separates from its underlying structure and before the test has reached a pull force of interest.

SUMMARY OF THE INVENTION

One object of this invention is to provide an adhesion test that can be performed on a wafer or a test sample representing a wafer and to avoid making this test at a later stage in the manufacture of the semiconductor structure.

Another object of this invention is to provide a stud pull test for a semiconductor layer in which the stud remains adhered to the layer for a greater test pull.

According to this invention a test sample is formed with an underlying structure and a film. This test sample is prepared for the attachment of a pull stud by process steps that include boiling the sample in a salt water solution for a suitable time. The stud is attached to the film with epoxy and this assembly is clamped and baked for a suitable time to form a bond. The stud pull test is then performed with significantly less likelihood that the stud will break from the film before the film breaks from the underlying structure.

THE DRAWING

THE TABLES

Table 1 shows the results of tests on test samples with several different films.

Table 2 shows test results organized to isolate the effects of four parameters on maximum adhesion stress.

The Preferred Embodiment

Figure 1:
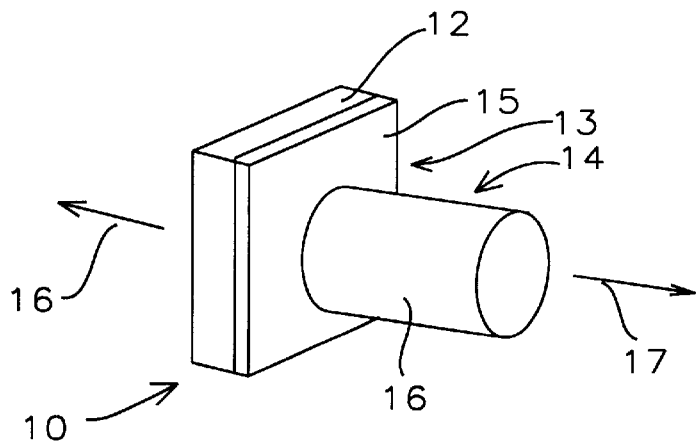
FIG. 1 is a diagram of a test sample for our pull test.

Introduction—FIG. 1

Our test can be performed on an actual circuit component, but preferably the test is performed on a test sample 10. The preferred samples have a substrate 12 and one or more films 13 formed on one surface of the substrate. We contemplate that a test will be made with a batch of several samples having identical substrates 12. The films 13 can be identical to provide more data about a given film and/or the films can differ in composition or processing for comparing one film with another. As is conventional, the samples 10 are identified at to the material and/or process for forming the film and the failure or success of a test can be attributed to the composition or processing of a particular film.

A stud 14 is attached to the exposed surface 15 of film 13 by epoxy 16 coating the stud, and a test is performed to pull apart substrate 12 and stud 14. The apparatus for the pull test is conventional and is represented in FIG. 1 by arrows 16 and 17 that point away from the sample and the stud.

As the force is increased during this test, the film 13 may delaminate from the substrate 12 (or two films may separate in a multi film test sample) or the test may be stopped at a preselected force before the film delaminates. The test apparatus signals the separating force during the test and at the time of any delamination. It is possible that the stud 14 will break away from its epoxy 16. Although it is possible that the stud epoxy 16 will separate from film 13, this event is much less likely than with stud pull tests of the prior art.

Figure 2:
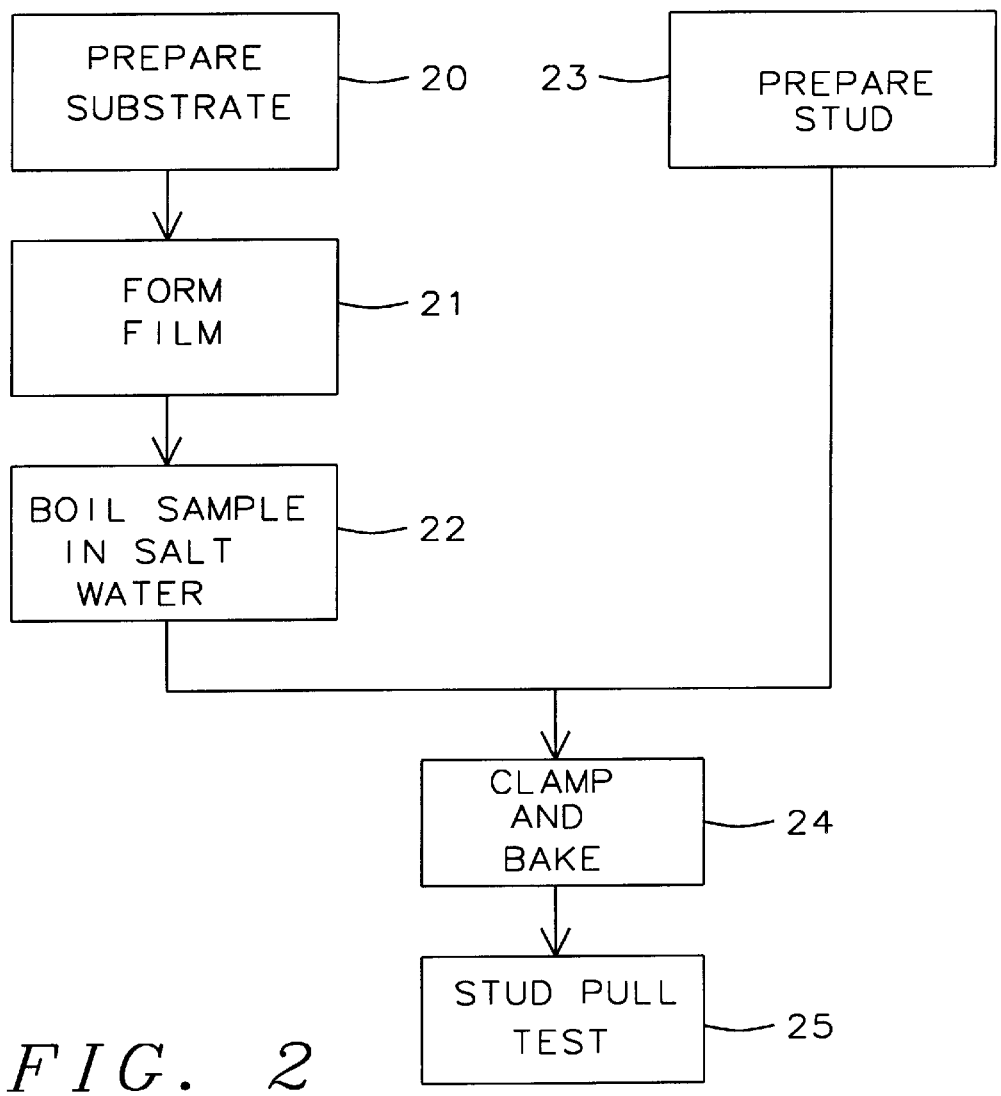
FIG. 2 is a flow chart showing the steps for preparing and testing a sample.

Preparing the Samples—FIG. 2

In the step identified by reference character 20, a substrate 12 is formed. The preferred substrate 12 is a metal square about 5 mm on a side. This structure simulates a metal layer of a semiconductor wafer except that the substrate 12 is given a suitable thickness to withstand the pull test. One commonly used metal its aluminum and it is suitable for the substrate. Other commonly used metals well known.

In step 21 in FIG. 2, a selected film 13 is formed on a surface of a substrate. The film is of a material that would be used in an actual semiconductor device, and it is formed by a production process that is otherwise being used in manufacturing wafers, by a process similar to such a production process, or by an experimental process that is to be investigated. Suitable films are well known and several are listed in Table 1.

Several substrates can be formed initially as a single piece of metal with a selected film and then cut into the individual test samples.

In step 22 in FIG. 2, the test sample is maintained in a boiling salt water solution for a suitable time. The preferred salt solution has a concentration of 15 grams of sodium chloride (NaCl) in 200 ml water, and the preferred time is 3.5 hours.

In step 23 in FIG. 2, a suitable stud 14 is given an epoxy coating. The preferred stud is a nail with a diameter of 0.106 inches. Step 23 can be performed at any time with respect to the sequence of steps 20, 21, and 22.

In step 24, the epoxy stud is clamped to the test sample with one surface contacting the surface of film 13. The clamped components are baked at a suitable temperature for a suitable time to bond the stud to the film. The preferred temperature is 150 C. and the preferred time is 3 hours.

In step 25, the samples are removed from the oven and the clamps are removed and the test samples are allowed to cool to room temperature. A sample is then placed in the pull test apparatus. As the prior art citations suggest, automated equipment is commonly used for the pull test. The tool slowly increases the pull force until the film delaminates from the substrate or the stud delaminates from its own epoxy.

TABLE 1

| Film Scheme | % film removed | Film delamination Force (Newtons) |
|---|---|---|
| 8KÅ USG | ~40% | 435 |
| 6KÅ FSG + N$_2$ + 2KÅ HDP USG | ~70% | 335 |
| 0.5KÅ PETEOS + 4KÅ HSQ + N$_2$ + 4KÅ PETEOS | ~60% | 235 |
| 0.5KÅ PEOX + 4KÅ HSQ + N$_2$ + 4KÅ PETOS | ~65% | 220 |
| 4KÅ HSQ + N$_2$ + 4KÅ PETEOS (Direct on Metal) | ~65% | 205 |
| 300Å SiON + 0.5KÅ PEOX + 4KÅ HSQ + N$_2$ + 4KÅ PETEOS | ~70% | 200 |
| 300Å SiON + 4KÅ HSQ + N$_2$ + 4KÅ PETEOS | ~80% | 175 |

Test Results—Table 1

The rows in Table 1 show the test results for seven different films. The salt concentration was 15 grams to 200 ml water, the boiling time was 3.5 hours, the stud diameter was 0.106 inches.

Five samples of each film were tested and the results were consistent and reproducible for each film. Other tests, still preliminary, showed a correlation between the results in Table 1 and the electrical characteristics of the corresponding wafers in the prior art test described earlier.

The left-most column gives information about the film. The abbreviations and acronyms in this column will be readily understood to define the films, primarily in terms of the process for forming the film. For example, PETEOS stands for "plasma enhanced TEOS" and TEOS stands for tetraethyl-orthosilicate" which is used as a source of oxygen in the plasma deposition of an oxide film. "K" stands for thousand for the thickness in Angstroms.

The right-most column gives the film delamination force in Newtons. This number is usually divided by the area of the stud contact to give the stud pull strength. Note that the films are listed by rank for film delamination force.

The second right-most column gives the percentage of the film that was removed during this test. A smaller number suggests that the adhesion is better and that a smaller portion of the film delaminated.

TABLE 2

| Name unit | Curing Time hours | Curing Temp Celsius | Cooking Time hours | Salt grams | Max Stress N |
|---|---|---|---|---|---|
| level-1 | 1 | 125 | 1 | 5 | |
| level-2 | 3 | 150 | 2.5 | 15 | |
| level-3 | 5 | 175 | 4 | 25 | |

TABLE 2-continued

| Name unit | Curing Time hours | Curing Temp Celsius | Cooking Time hours | Salt grams | Max Stress N |
|---|---|---|---|---|---|
| run #1 | 1 | 125 | 1 | 5 | 309 |
| run #2 | 1 | 150 | 2.5 | 15 | 254.62 |
| run #3 | 1 | 175 | 4 | 25 | 221.7 |
| run #4 | 3 | 125 | 2.5 | 25 | 280 |
| run #5 | 3 | 150 | 4 | 5 | 145.96 |
| run #6 | 3 | 175 | 1 | 15 | 283.87 |
| run #7 | 5 | 125 | 4 | 15 | 167.5 |
| run #8 | 5 | 150 | 1 | 25 | 356.8 |
| run #9 | 5 | 175 | 2.5 | 5 | 284.6 |
| run #10 | 1 | 125 | 1 | 5 | 309 |

Test Results—Table 2

Table 2 shows the process and the test results for several test samples. The uppermost row of Table 2 has identifiers for the columns of the table and the second row gives the units for the numerals in the columns. Each other row gives the parameters for one test. The left-most column for these other rows (Name) has arbitrary names for the tests.

Columns Curing Time and Curing Temp give these parameters for the step of baking the clamped stud and test sample, step 24 in FIG. 2.

Columns Cooking Time and Salt give the parameters for boiling the test sample in a salt water solution, step 22 in FIG. 2. Column Max Stress gives the results of the stud pull test on the sample.

Figure 3:
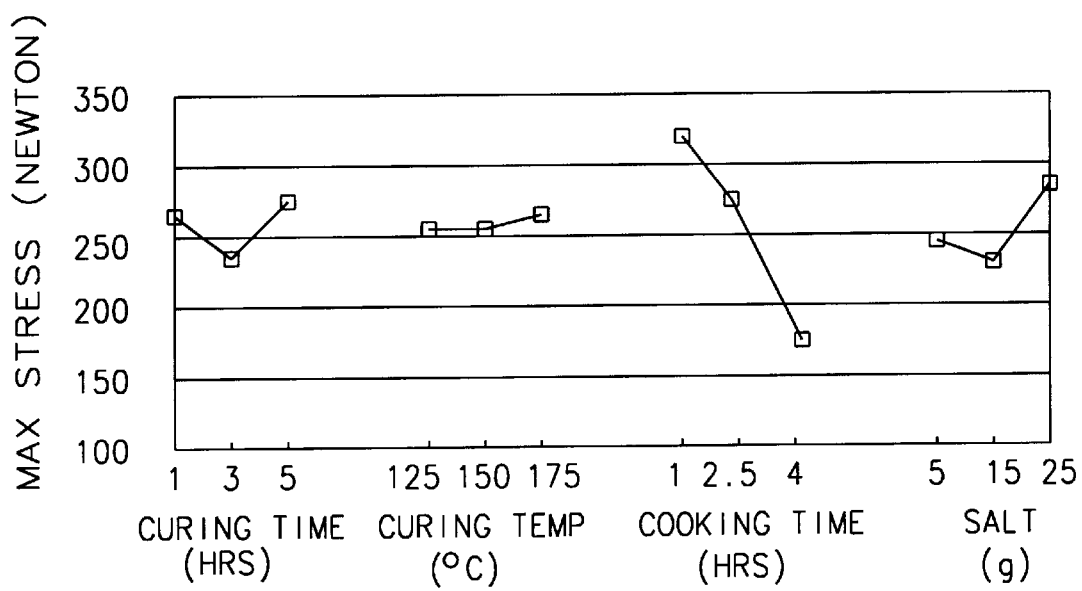
FIG. 3 is a plot of the maximum adhesion stress for samples prepared with variations in four parameters.

Test Results—FIG. 3

FIG. 3 presents this data in the form of four plots that are organized with a common vertical axis, maximum stress in Newtons. They have individual values along the horizontal axis and a legend that identifies the parameter. For example, the left-most plot shows curing time for 1 hour, 3 hours, and 5 hours.

Other Embodiments

From our description of the preferred embodiment, those skilled in the art will recognize modifications within the spirit of the invention and the scope of the claims.

What is claimed is:

1. A method for testing the adhesion of a selected film and a substrate underlying the film, comprising the following steps, preparing a test sample having the substrate and film, maintaining the sample in a boiling solution of salt water for a selected time, providing an epoxy coated pull stud, clamping the pull stud to the film of the test sample, and baking the stud and sample at a selected temperature while maintaining the stud clamped to the sample test sample for a selected time to attach the stud to the film, cooling the test sample and removing the clamp, and slowly pulling the stud from the sample until the film breaks from the substrate or the stud breaks from the epoxy bonding the stud to the film.

2. The testing method of claim 1 wherein the salt solution has a concentration of about 15 grams of sodium chloride for 200 ml of water.

3. The testing method of claim 2 wherein the selected time for maintaining the sample in a boiling solution of salt water is in the range of 1 to 4 hours.

4. The testing method of claim 3 wherein the selected time for maintaining the sample in a boiling solution of salt water is about 3.5 hours.

5. The method of claim 3 wherein the substrate is a metal.

6. The method of claim 5 wherein the substrate is in the shape of a square of a selected length on a side and of a thickness selected for the pull test.

7. The method of claim 6 wherein the sample is about 5 millimeters on a side.

8. The method of claim 7 wherein the metal substrate is initially of a size for forming a plurality of samples and the step of preparing the test sample includes slicing the initial substrate into a plurality of samples with sides of a selected length.

9. The method of claim 6 wherein the selected time for baking the stud and sample to attach the stud to the film is a few hours.

10. The method of claim 9 wherein the selected time is about three hours.

11. The method of claim 10 wherein the selected temperature is about 150 degrees Celsius.

* * * * *